United States Patent [19]
Patel

[11] 3,954,109
[45] May 4, 1976

[54] BANDAGE TO PREVENT LOCAL HEMATOMA

[75] Inventor: Harish A. Patel, Oak Park, Ill.

[73] Assignee: The Kendall Company, Walpole, Mass.

[22] Filed: Aug. 2, 1974

[21] Appl. No.: 494,106

[52] U.S. Cl. .................................................. 128/327
[51] Int. Cl.² ........................................ A61B 17/12
[58] Field of Search ............ 128/155, 156, 169, 170, 128/171, 296, 325, 326, 327, 335, 341

[56] References Cited
UNITED STATES PATENTS

| 438,929 | 10/1890 | Knight | 128/341 |
|---|---|---|---|
| 2,152,922 | 4/1939 | Robinson | 128/327 |
| 2,185,571 | 1/1940 | Robinson | 128/327 |
| 2,196,296 | 4/1940 | Flynn | 128/335 |
| 2,387,131 | 10/1945 | Fernandez | 128/355 |
| 2,421,193 | 5/1947 | Gardner | 128/335 |
| 3,157,178 | 11/1964 | Bentov | 128/296 X |
| 3,171,410 | 3/1965 | Towle, Jr. et al. | 128/155 |

FOREIGN PATENTS OR APPLICATIONS

| 289,014 | 7/1927 | United Kingdom | 128/155 |

*Primary Examiner*—Channing L. Pace
*Attorney, Agent, or Firm*—Powell L. Sprunger

[57] ABSTRACT

A bandage to prevent local hematoma adjacent a puncture site on a patient comprising, pad means for placement over the puncture site, with the pad means being expansible responsive to contact by liquid. The bandage also has means for securing the pad means over the puncture site and for applying pressure with the pad means to the site.

32 Claims, 9 Drawing Figures

U.S. Patent    May 4, 1976    3,954,109
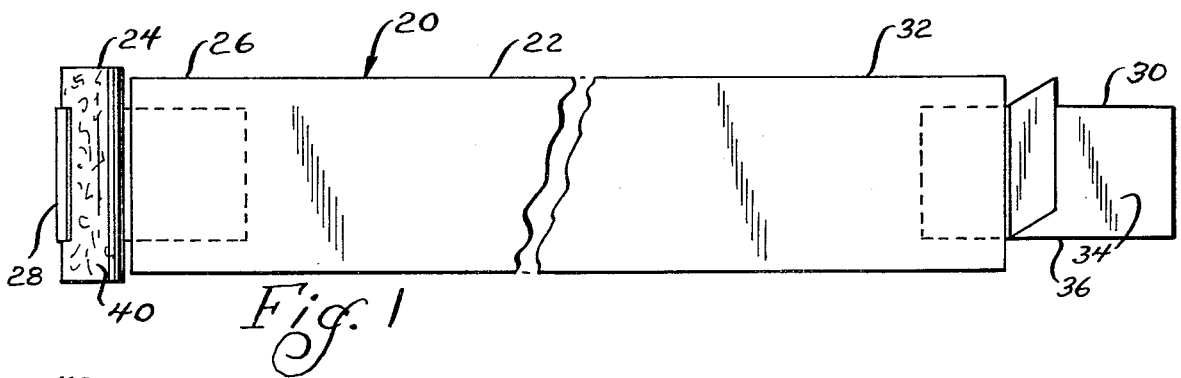
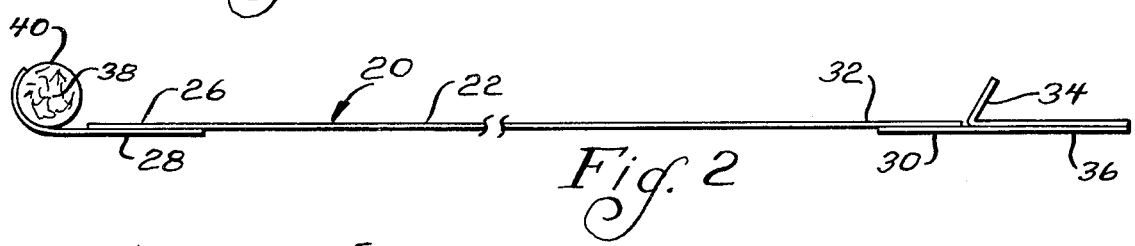
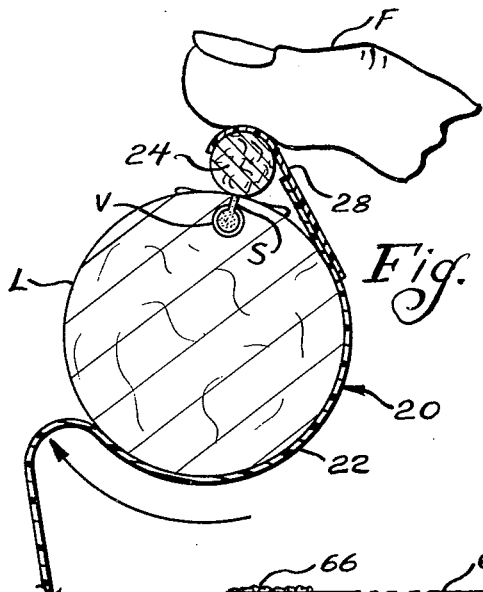
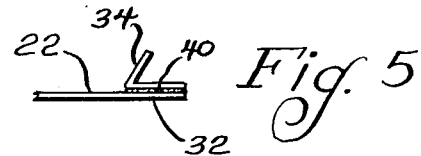
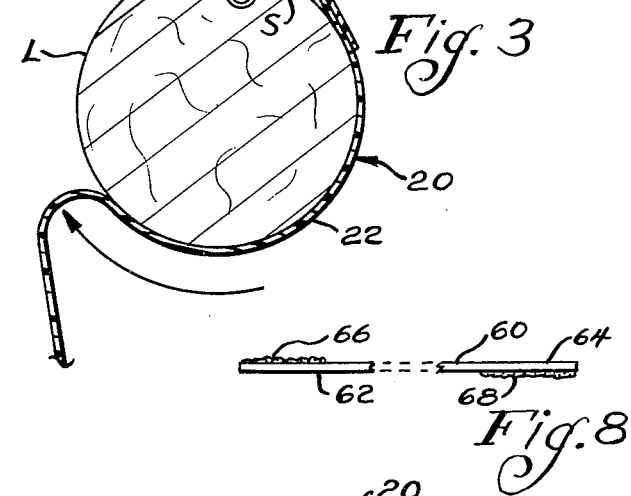
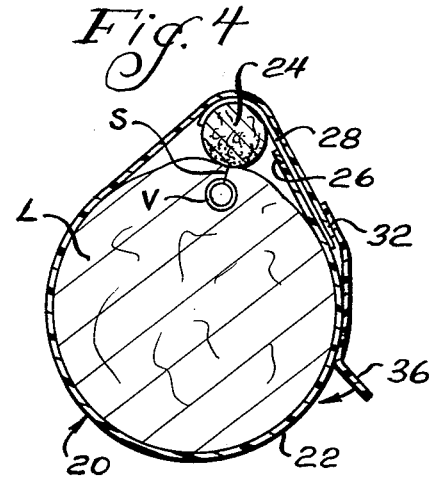
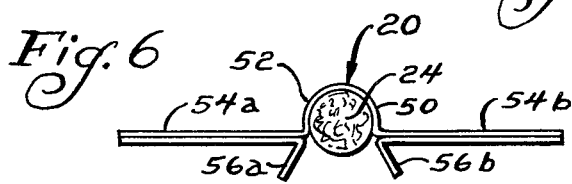
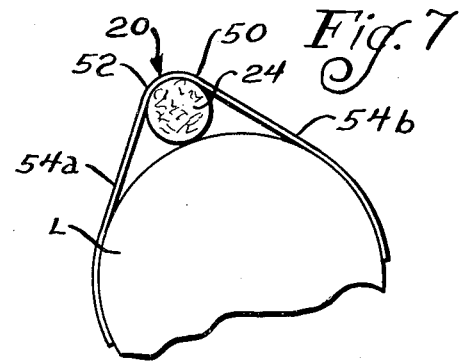
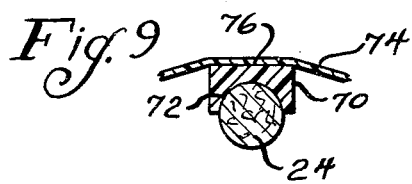

BANDAGE TO PREVENT LOCAL HEMATOMA

BACKGROUND OF THE INVENTION

The present invention relates to bandages, and more particularly to pressure bandages.

It is a common procedure to aspirate arterial blood with a needle and syringe to obtain a blood sample. After removal of the needle from the blood vessel, it is the recommended procedure in a hospital for the attendant, such as a nurse, to apply pressure to the site for approximately five minutes. Other than for special patients, pressure is applied to the site not necessarily to prevent bleeding, but to prevent a local hematoma.

Normally blood will pass from the vessel through the puncture site to the skin where it will clot. However, if pressure is not applied to the puncture site, blood will collect subcutaneously, and if contaminated through blood adjacent the skin, could lead to a local hematoma, resulting in soreness at the puncture site. In unusual situations, where unattended, the local hematoma may lead to septicemia, a possible morbid condition. Thus, pressure is applied to the puncture site to prevent the subcutaneous collection of blood and local hematoma, without applying sufficient pressure to cut off circulation of blood.

Certain patients, for example, diabetics and hemophiliacs, may continue to bleed if left unattended. Some patients may be placed on a heparin therapy after cardio-vascular surgery, and will continue to bleed after aspiration of arterial or venous blood, samples of which are periodically necessary for analysis. Sometimes the susceptibility of the patient to excessive bleeding is unknown, and pressure is applied to the puncture site as a precaution to determine whether prolonged bleeding will be present.

SUMMARY OF THE INVENTION

A principal feature of the present invention is the provision of a bandage for applying controlled pressure to a puncture site.

The bandage of the present invention includes an absorbent pad means for placement over the puncture site, with the pad means being expansible responsive to wetting by liquid. The bandage also has means for securing the pad means over the puncture site and for applying pressure with the pad means against the site.

A feature of the present invention is that the pad means applies pressure to the puncture site responsive to bleeding from the site.

Another feature of the invention is that the amount of pressure applied by the pad means to the puncture site after placement is generally proportional to the extent of bleeding from the site.

Yet another feature of the invention is that the bandage of the present invention eliminates the need for an attendant to apply digital pressure to the puncture site after aspiration of blood.

Further features become more fully apparent in the following description of the embodiments of this invention and from the appended claims.

DESCRIPTION OF THE DRAWINGS

In the drawings:

FIG. 1 is a fragmentary plan view of one embodiment of the bandage of the present invention;

FIG. 2 is a fragmentary elevational view of the bandage of FIG. 1;

FIG. 3 is a fragmentary sectional view illustrating a step in the wrapping of the bandage of FIG. 1 about a patient's limb;

FIG. 4 is a sectional view of the bandage of FIG. 3 as wrapped about the patient's limb;

FIG. 5 is a fragmentary elevational view of another embodiment of a band for the bandage of FIG. 1;

FIG. 6 is an elevational view of another embodiment of the bandage of the present invention;

FIG. 7 is a plan view, taken partly in section, of the bandage of FIG. 6 as wrapped on a limb of the patient;

FIG. 8 is a fragmentary elevational view of another embodiment of a band for the bandage of the present invention; and FIG. 9 is a fragmentary sectional view of another embodiment of a pad structure for the bandage of the present invention.

DESCRIPTION OF THE PREFERRED EMBODIMENTS

Referring now to FIGS. 1 and 2, there is shown a pressure bandage generally designated 20 having a flexible band 22 and an absorbent pad or pad means 24 secured to one end 26 of the band by an adhesive bearing tape strip 28. The bandage 20 has a tape strip 30 extending from the other end 32 of the band 22, with a release sheet 34 covering the adhesive on an extending end portion 36 of the tape strip 30.

The flexible band may be made of any suitable material elastic or non-elastic, such as Tyvek, a trademark of E. I. du Pont de Nemours, a nonwoven, or cloth. The band 22 has a length sufficient to extend around the limb of a patient for a purpose which will be described below. The absorbent pad 24 is of the type which expands responsive to wetting by liquid, such as blood, and preferably generally proportional to the amount of wetting which takes place. A suitable pad for the bandage of the present invention may be a tampon sold by various companies, such as the tampon Tampax, a trademark of Tampax Corporation or Kotex, a trademark of Kimberly-Clark Corporation. The inner portion 38 of the pad may be made of a mass of organic fibers, such as slightly compressed cotton linters, or a compressed mixture of cotton linters and tubular fibers, such as rayon, and may be relatively rigid. In the latter case, the cotton linters provide absorbency to the pad, and the tubular fibers provide springiness to the pad when wetted. Another suitable structure for the pad may be a compressed synthetic foam or natural sponge material. Additionally, a compressed dehydrated material, such as cellulose may be used. The inner portion of the pad may be wrapped with a cover 40 of a nonwoven material to maintain the structural integrity of the pad. The pad 24 preferably has a cylindrical shape, but other suitable shapes for the pad may include elliptical, rectangular, triangular or polygonal. Where the pad has a planar surface for facing the patient's skin, the surface preferably has a relatively narrow width.

After aspiration of blood from a vessel V of a patient's limb L, as illustrated in FIG. 3, the absorbent pad 24 is placed over the puncture site S which is defined by the aspirating needle after removal, and a slight pressure is exerted by the attendant's finger F against the pad 24 over the site S. Next, the band 22 of the bandage is wrapped around the limb, as indicated by the direction of the arrow in FIG. 3. The attendant's finger F is removed from the absorbent pad 24 as the band 22 is wound over the outer portion of the pad, and the other end 32 of the band 22 is secured in place on the outer surface of the band with the tape strip 36, as shown in FIG. 4.

As thus placed, the bandage 20 applies pressure with the absorbent pad 24 against the puncture site S leading to the vessel V. Accordingly, the bandage provides an immediate closure for the puncture site S, and initially may provide sufficient pressure against the puncture site S to stop bleeding and close a channel V by counterpressure defined by the puncture at the site. However, if there is a continued bleeding from the site, the blood enters the absorbent pad, and the pad expands somewhat due to the wetting, thus placing additional pressure against the site, since the band offers more resistance to expansion than the tissue underlying the skin. Bleeding from the patient and expansion of the pad 24 may continue until the puncture site is completely closed, thus stopping the bleeding, as shown in FIG. 4. Moreover, closure of the puncture site by the applied pressure prevents subcutaneous bleeding, and a possible local hematoma resulting from such bleeding, since the counterpressure extends to the artery itself. After the bandage has been placed, as described, the attendant may leave the locality of the patient, and return in approximately five minutes to check and remove the bandage. If the patient is normal, the bleeding will have stopped, and subcutaneous bleeding and local hematoma will have been prevented. If the patient continues to bleed after removal of the bandage, the attendant will be apprised that the patient is susceptible to a bleeding condition, such as hemophilia, and may take appropriate action such as reapplying the bandage. Accordingly, the pressure bandage of the present invention prevents the formation of local hematoma, and frees the attendant for other duties while pressure is being applied to the puncture site in a safe manner.

Another embodiment of the bandage of the present invention is illustrated in FIG. 5, in which adhesive 40 is located on the band 22 adjacent its other end 32. The adhesive 40 on the band is covered by a release sheet 34, which is removed during placement of the bandage on the patient's limb, as described in connection with the bandage of FIGS. 1–4.

Another embodiment of the bandage of the present invention is illustrated in FIGS. 6 and 7, which is particularly useful for placement on a limb of larger dimensions where aspiration has taken place, such as the femoral artery in the thigh. As illustrated in FIG. 6, the bandage 20 has an absorbent pad 24, as described in connection with FIGS. 1–4, and an adhesive bearing tape strip 50 having a medial portion 52 attached to the pad 24, and end portions 54a and 54b extending on opposite sides of the pad 24. A pair of release sheets 56a and 56b cover the adhesive on the tape end portions 54a and b.

In use, the absorbent pad 24 is placed over the puncture site with the appropriate amount of digital pressure, and the release sheets 56a and b are removed from the end portions 54a and b of the strip 50, after which the end portions 54a and b are attached to the patient's limb L, as shown in FIG. 7. The bandage of FIGS. 6 and 7 operates in a manner similar to the bandage of FIGS. 1–4 in applying pressure and closing the puncture site to prevent subcutaneous bleeding and local hematoma of the patient.

Another embodiment of a band 60 for securing the absorbent pad to the patient is illustrated in FIG. 8, in which the pad (not shown) is secured to the band intermediate its outer ends 62 and 64, or adjacent an end, as desired. The band has a sufficient length to extend around the limb of the patient, and has a cohesive material 66 and 68, such as latex, located on opposed surfaces of the band ends 62 and 64. During placement of the bandage, the ends of the band are wrapped about the patient's limb and secured together by the cohesive material 66 and 68 to retain the bandage in place. It is apparent that many other securing means may be used to retain the pad in position, such as a tie extending from the pad and having a sufficient length to extend around the patient's limb, such that the ends of the tie may be tied together about the limb.

In FIG. 9 there is shown a retaining member 70 having a recess 72 to receive and hold the pad 24. A band 74 is secured to a generally planar surface 76 of the retaining member 70 remote the pad 24, such that the retaining member stabilizes the pad to apply even pressure against the patient when the band is secured to the patient's limb.

The foregoing detailed description is given for clearness of understanding only, and no unnecessary limitations should be understood therefrom, as modifications will be obvious to those skilled in the art.

I claim:

1. A pressure bandage to prevent local hematoma adjacent a puncture site in a patient, comprising:
   absorbent pad means for placement over the puncture site, said pad means being expansible in a direction applying pressure against the site when confined over the site, said expansibility being responsive to wetting by liquid from the site; and
   means for securing the pad means over the puncture site and for applying an initial pressure with the pad means against the site, said pad means expanding and applying an additional pressure against the site dependent upon the amount of liquid passing from the site.

2. The bandage of claim 1 wherein said pad means has a generally cylindrical shape.

3. The bandage of claim 1 wherein said pad means comprises a compressed mixture of cotton linters and rayon fibers.

4. The bandage of claim 1 wherein said pad means comprises a slightly compressed mass of cotton linters.

5. The bandage of claim 1 wherein said pad means comprises a compressed mass of foam material.

6. The bandage of claim 1 wherein said pad means comprises a compressed mass of sponge material.

7. The bandage of claim 1 wherein said pad means comprises a compressed mass of dehydrated material.

8. The bandage of claim 1 wherein pad means includes a cover of nonwoven material.

9. The bandage of claim 1 wherein the securing and applying means comprises a band of flexible material attached to said pad means.

10. The bandage of claim 9 wherein said band has one end attached to said pad means.

11. The bandage of claim 10 including tape means for securing said pad means to the one band end.

12. The bandage of claim 10 wherein said band includes adhering means adjacent the other end of the band for securing the band during placement of the bandage.

13. The bandage of claim 12 including a release sheet covering said adhering means.

14. The bandage of claim 9 wherein said band has a sufficient length to extend completely around a limb of the patient.

15. The bandage of claim 14 including a pair of spaced zones of a cohesive material on the band for securing the band about the patient's limb.

16. The bandage of claim 15 wherein the pad means is positioned intermediate the ends of the band and the cohesive zones are located on opposed surfaces of the band adjacent the opposite band ends.

17. The bandage of claim 9 wherein said band is made from an elastic material.

18. The bandage of claim 9 wherein said band is made from a non-elastic material.

19. The bandage of claim 9 wherein said band is made from a nonwoven material.

20. The bandage of claim 9 wherein said pad means is elongated and aligned laterally relative the length of said band.

21. The bandage of claim 9 including a retaining member secured to the pad means, said retaining member having a generally planar surface remote the pad means secured to said band.

22. The bandage of claim 1 wherein the securing and applying means comprises tape means attached to said pad means and extending on opposite sides of the pad means.

23. The bandage of claim 22 including a pair of release sheets covering adhesive on the opposed sides of the tape means.

24. The bandage of claim 1 wherein the amount of expansion of said pad means is generally proportional to the quantity of liquid wetting the pad means.

25. A pressure bandage to prevent local hematoma adjacent a puncture site in a patient, comprising:
    absorbent pad means for placement over the puncture site and expansible in a direction applying pressure against the site responsive to wetting by liquid from the puncture site;
    an elongated flexible band having one end attached to said pad means, said band having a sufficient length to extend around the limb of a patient for wrapping the limb and applying pressure to the pad means; and
    adhering means adjacent the other end of the band for securing the other end of the band to the outer surface of the band after placement of the pad means and wrapping the band about the limb of the patient.

26. The bandage of claim 25 including a release sheet covering said adhering means.

27. The bandage of claim 25 wherein said adhering means comprises a tape strip extending from the other end of the band.

28. The bandage of claim 27 wherein said adhering means comprises adhesive on the band adjacent its other end.

29. A pressure bandage to prevent local hematoma adjacent a puncture site in a patient, comprising:
    absorbent pad means for placement over the puncture site and expansible in a direction applying pressure against the site, said expansibility being responsive to wetting by liquid passing from the puncture site; and
    a tape strip having a medial portion attached to said pad means and having end portions extending on opposite sides of the pad means for securing the pad means over the puncture site and placing pressure with the pad means against the site.

30. The bandage of claim 29 including a pair of release sheets covering the end portions of said tape strip.

31. A pressure bandage for a puncture site in a patient, comprising:
    absorbent pad means for applying a variable amount of increased pressure to the site responsive to the extent of bleeding from the site; and
    means for securing the pad means over the site.

32. A pressure bandage for a puncture site in a patient comprising:
    relatively rigid expansible pad means for placement in facing contact with the puncture site, said pad means expanding in a direction applying pressure against the site responsive to liquid passing from the site; and
    means for securing the pad means over the puncture site and for applying pressure with the pad means against the site.

* * * * *